(12) United States Patent
Besman et al.

(10) Patent No.: US 9,352,027 B2
(45) Date of Patent: *May 31, 2016

(54) ALBUMIN-FREE FACTOR VIII FORMULATIONS

(71) Applicant: Baxter International Inc., Deerfield, IL (US)

(72) Inventors: Marc Besman, Studio City, CA (US); Erik Bjornson, Studio City, CA (US); Feroz Jameel, Covina, CA (US); Ramesh Kashi, Walnut, CA (US); Michael Pikal, Mansfield Center, CT (US); Serguei Tchessalov, Ashford, CT (US); John Carpenter, Littleton, CO (US)

(73) Assignees: Baxalta Incorporated, Bannockburn, IL (US); Baxalta GmbH, Glattpark (Opfikon); University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,391

(22) Filed: May 23, 2014

(65) Prior Publication Data

US 2015/0025010 A1    Jan. 22, 2015

Related U.S. Application Data

(60) Continuation of application No. 13/760,900, filed on Feb. 6, 2013, now Pat. No. 8,765,665, which is a continuation of application No. 13/250,789, filed on Sep. 30, 2011, now Pat. No. 8,372,800, which is a continuation of application No. 11/764,770, filed on Jun. 18, 2007, now Pat. No. 8,058,226, which is a continuation of application No. 11/434,634, filed on May 15, 2006, now Pat. No. 7,247,707, which is a division of application No. 10/610,723, filed on Jul. 1, 2003, now Pat. No. 7,087,723, which is a continuation of application No. 09/507,011, filed on Feb. 22, 2000, now Pat. No. 6,586,573, which is a continuation-in-part of application No. 09/452,752, filed on Dec. 1, 1999, now abandoned, which is a continuation-in-part of application No. 09/255,279, filed on Feb. 22, 1999, now abandoned.

(51) Int. Cl.
| | |
|---|---|
| A61K 38/37 | (2006.01) |
| A61K 9/00 | (2006.01) |
| A61K 9/19 | (2006.01) |
| A61K 47/02 | (2006.01) |
| A61K 47/10 | (2006.01) |
| A61K 47/18 | (2006.01) |
| A61K 47/38 | (2006.01) |
| A61K 47/26 | (2006.01) |

(52) U.S. Cl.
CPC ............... *A61K 38/37* (2013.01); *A61K 9/0019* (2013.01); *A61K 9/19* (2013.01); *A61K 47/02* (2013.01); *A61K 47/10* (2013.01); *A61K 47/18* (2013.01); *A61K 47/183* (2013.01); *A61K 47/26* (2013.01); *A61K 47/38* (2013.01); *Y10S 514/834* (2013.01); *Y10S 530/829* (2013.01)

(58) Field of Classification Search
None
See application file for complete search history.

(56) References Cited

U.S. PATENT DOCUMENTS

| | | |
|---|---|---|
| 3,770,631 A | 11/1973 | Fekete et al. |
| 3,839,314 A | 10/1974 | Fekete et al. |
| 3,893,990 A | 7/1975 | Fekete et al. |
| 3,893,991 A | 7/1975 | Fekete et al. |
| 3,980,432 A | 9/1976 | Trobisch |
| 4,027,013 A | 5/1977 | Bick et al. |
| 4,069,216 A | 1/1978 | Shanbrom |
| 4,073,886 A | 2/1978 | Kehn |
| 4,085,095 A | 4/1978 | Bick et al. |
| 4,086,218 A | 4/1978 | Shanbrom et al. |
| 4,089,944 A | 5/1978 | Thomas |
| 4,105,650 A | 8/1978 | Shanbrom et al. |

(Continued)

FOREIGN PATENT DOCUMENTS

| | | |
|---|---|---|
| CA | 1 187 410 A1 | 5/1985 |
| CA | 2 065 553 C | 6/2003 |

(Continued)

OTHER PUBLICATIONS

US 5,659,014, 8/1997, Bhattacharya (withdrawn).

(Continued)

*Primary Examiner* — Maury Audet
(74) *Attorney, Agent, or Firm* — Morgan, Lewis & Bockius LLP

(57) ABSTRACT

A Factor VIII composition formulated without albumin, comprising the following formulation excipients in addition to Factor VIII: 4% to 10% of a bulking agent selected from the group consisting of mannitol, glycine and alanine; 1% to 4% of a stabilizing agent selected from the group consisting of sucrose, trehalose, raffinose, and arginine; 1 mM to 5 mM calcium salt; 100 mM to 300 mM NaCl; and a buffering agent for maintaining a pH of approximately between 6 and 8. Alternatively, the formulation can comprise 2% to 6% hydroxyethyl starch; 1% to 4% of a stabilizing agent selected from the group consisting of sucrose, trehalose, raffinose, and arginine; 1 mM to 5 mM calcium salt; 100 mM to 300 mM NaCl; and a buffering agent for maintaining a pH of approximately between 6 and 8. In a further embodiment, the formulation can comprise: 300 mM to 500 mM NaCl; 1% to 4% of a stabilizing agent selected from the group consisting of sucrose, trehalose, raffinose, and arginine; 1 mM to 5 mM calcium salt; and a buffering agent.

10 Claims, No Drawings

(56) References Cited

U.S. PATENT DOCUMENTS

| | | |
|---|---|---|
| 4,137,223 A | 1/1979 | Shanbrom et al. |
| 4,189,425 A | 2/1980 | Shanbrom et al. |
| 4,229,435 A | 10/1980 | Blomback et al. |
| 4,297,344 A | 10/1981 | Schwinn et al. |
| 4,327,086 A | 4/1982 | Fukushima |
| 4,341,764 A | 7/1982 | Wallace |
| 4,370,264 A | 1/1983 | Kotitschke et al. |
| 4,382,083 A | 5/1983 | Thomas |
| 4,386,068 A | 5/1983 | Mitra |
| 4,387,092 A | 6/1983 | Liautaud et al. |
| 4,404,131 A | 9/1983 | Schwarz et al. |
| 4,440,679 A | 4/1984 | Fernandes et al. |
| 4,446,134 A | 5/1984 | Naito et al. |
| 4,455,301 A | 6/1984 | Mitra et al. |
| 4,479,938 A | 10/1984 | Thomas |
| 4,481,189 A | 11/1984 | Prince |
| 4,495,175 A | 1/1985 | Chavin |
| 4,495,278 A | 1/1985 | Thomas |
| 4,522,751 A | 6/1985 | Linnau |
| 4,540,573 A | 9/1985 | Neurath et al. |
| 4,543,210 A | 9/1985 | Mitra et al. |
| 4,562,072 A | 12/1985 | Heimburger et al. |
| 4,591,505 A | 5/1986 | Prince |
| 4,613,501 A | 9/1986 | Horowitz |
| 4,623,717 A | 11/1986 | Fernandes et al. |
| 4,640,834 A | 2/1987 | Eibl et al. |
| 4,650,858 A | 3/1987 | Rasmussen |
| 4,693,981 A | 9/1987 | Wiesehahn |
| 4,727,027 A | 2/1988 | Wiesehahn et al. |
| 4,739,039 A | 4/1988 | Vasquez et al. |
| 4,743,680 A | 5/1988 | Mathews et al. |
| 4,748,120 A | 5/1988 | Wiesehahn |
| 4,758,657 A | 7/1988 | Farb et al. |
| 4,783,441 A | 11/1988 | Thurow |
| 4,795,806 A | 1/1989 | Brown et al. |
| 4,803,073 A | 2/1989 | Doleschel et al. |
| 4,814,435 A | 3/1989 | Schwarz |
| 4,831,012 A | 5/1989 | Estep |
| 4,841,023 A | 6/1989 | Horowitz |
| 4,847,362 A | 7/1989 | Mathews et al. |
| 4,849,508 A | 7/1989 | Magnin et al. |
| 4,876,241 A | 10/1989 | Feldman et al. |
| 4,877,608 A | 10/1989 | Lee et al. |
| 4,891,319 A | 1/1990 | Roser |
| 4,946,648 A | 8/1990 | Dichtelmuller et al. |
| 4,952,675 A | 8/1990 | Mathews et al. |
| 4,960,757 A | 10/1990 | Kumpe et al. |
| 4,981,951 A | 1/1991 | Tsay |
| 5,043,428 A | 8/1991 | Heimburger et al. |
| 5,047,249 A | 9/1991 | Rothman |
| 5,051,353 A | 9/1991 | Stratton |
| 5,116,950 A | 5/1992 | Miyano et al. |
| 5,138,034 A | 8/1992 | Uemura |
| 5,177,191 A | 1/1993 | Brockway et al. |
| 5,180,583 A | 1/1993 | Hedner |
| 5,192,743 A | 3/1993 | Hsu et al. |
| 5,232,844 A | 8/1993 | Horowitz et al. |
| 5,245,014 A | 9/1993 | Kaersgaard |
| 5,252,709 A | 10/1993 | Burnouf et al. |
| 5,252,710 A | 10/1993 | Dazey et al. |
| 5,254,350 A | 10/1993 | Barrow |
| 5,259,951 A | 11/1993 | Arrighi et al. |
| 5,272,135 A | 12/1993 | Takruri |
| 5,288,853 A | 2/1994 | Bhattacharva et al. |
| 5,304,638 A | 4/1994 | Marshall et al. |
| 5,328,694 A | 7/1994 | Schwinn |
| 5,356,878 A | 10/1994 | Brockway et al. |
| 5,371,195 A | 12/1994 | Grandgeorge et al. |
| 5,378,601 A | 1/1995 | Gepner-Puszkin |
| 5,378,612 A | 1/1995 | Nakashima et al. |
| 5,399,670 A | 3/1995 | Bhattacharya et al. |
| 5,408,039 A | 4/1995 | Burnouf-Radosevich |
| 5,410,022 A | 4/1995 | Eibl et al. |
| 5,418,130 A | 5/1995 | Platz et al. |
| 5,424,401 A | 6/1995 | Heimburger et al. |
| 5,439,882 A | 8/1995 | Feola |
| 5,514,781 A | 5/1996 | Dobkin |
| 5,565,427 A | 10/1996 | Freudenberg |
| 5,580,856 A | 12/1996 | Prestrelski et al. |
| 5,587,490 A | 12/1996 | Goodrich, Jr. |
| 5,605,884 A | 2/1997 | Lee et al. |
| 5,679,549 A | 10/1997 | Chan |
| 5,679,776 A | 10/1997 | Burnouf-Radosevich |
| 5,693,499 A | 12/1997 | Yonemura et al. |
| 5,712,086 A | 1/1998 | Horowitz et al. |
| 5,733,873 A * | 3/1998 | Osterberg et al. ............ 514/13.7 |
| 5,760,183 A | 6/1998 | Dazey et al. |
| 5,763,401 A | 6/1998 | Nayar |
| 5,780,295 A | 7/1998 | Livesey |
| 5,798,238 A | 8/1998 | Goodrich, Jr. |
| 5,851,800 A | 12/1998 | Adamson |
| 5,858,375 A | 1/1999 | Furminger |
| 5,874,408 A | 2/1999 | Nayar |
| 5,919,443 A | 7/1999 | Michaelis et al. |
| 5,919,908 A | 7/1999 | Osterberg et al. |
| 5,955,448 A | 9/1999 | Colaco |
| 6,005,082 A | 12/1999 | Smeds |
| 5,565,427 C1 | 7/2002 | Freudenberg |
| 6,440,414 B1 | 8/2002 | Kendrick et al. |
| 6,586,573 B1 * | 7/2003 | Besman et al. ................ 530/383 |
| 6,599,724 B1 | 7/2003 | Mikaelsson et al. |
| 6,649,386 B2 | 11/2003 | Roser |
| 7,087,723 B2 * | 8/2006 | Besman et al. ................ 530/383 |
| 7,247,707 B2 * | 7/2007 | Besman et al. ................ 530/383 |
| 8,058,226 B2 * | 11/2011 | Besman et al. ................ 514/1.1 |
| 8,372,800 B2 * | 2/2013 | Besman et al. ................ 514/1.1 |
| 8,765,665 B2 * | 7/2014 | Besman et al. ................ 514/1.1 |

FOREIGN PATENT DOCUMENTS

| | | |
|---|---|---|
| CN | 1047342 A | 11/1990 |
| DE | 3904354 A1 | 8/1990 |
| DE | 4431833 C1 | 9/1994 |
| EP | 0 117 064 A2 | 8/1984 |
| EP | 0 123 945 A1 | 11/1984 |
| EP | 0 127 025 A2 | 12/1984 |
| EP | 0 131 740 A2 | 1/1985 |
| EP | 0 137 428 A2 | 4/1985 |
| EP | 0 171 506 A1 | 2/1986 |
| EP | 0 209 041 A2 | 1/1987 |
| EP | 0 237 981 A2 | 9/1987 |
| EP | 0 077 870 B1 | 7/1989 |
| EP | 0 212 040 B1 | 5/1990 |
| EP | 0 399 321 A2 | 11/1990 |
| EP | 0 410 207 A2 | 1/1991 |
| EP | 0 035 204 B2 | 5/1991 |
| EP | 0 229 810 B | 10/1991 |
| EP | 0 468 181 A2 | 1/1992 |
| EP | 0 315 968 B2 | 5/1992 |
| EP | 0 150 735 B1 | 7/1992 |
| EP | 0 508 194 A1 | 10/1992 |
| EP | 0 314 095 B1 | 12/1992 |
| EP | 0 306 968 B1 | 12/1993 |
| EP | 0 292 003 B1 | 3/1994 |
| EP | 0 600 480 A2 | 6/1994 |
| EP | 0 383 234 B1 | 11/1994 |
| EP | 0 410 207 B1 | 1/1997 |
| EP | 0 771 567 A1 | 5/1997 |
| EP | 0 818 204 A2 | 1/1998 |
| GB | 941019 A | 4/1961 |
| GB | 2085729 A | 5/1982 |
| GB | 2129685 A | 5/1984 |
| JP | 56-127308 A | 10/1981 |
| JP | 60199829 A | 10/1985 |
| JP | 61022022 A | 1/1986 |
| JP | 61-271222 A | 12/1986 |
| JP | 62195331 A | 8/1987 |
| JP | 64-075431 A | 3/1989 |
| JP | 01-149733 A | 6/1989 |
| JP | 01-157917 A | 6/1989 |
| JP | 02-157231 A | 6/1990 |
| JP | 05-331071 A | 12/1993 |
| JP | 08-053361 A | 2/1996 |
| JP | 8-504784 A | 5/1996 |

(56) References Cited

FOREIGN PATENT DOCUMENTS

| | | |
|---|---|---|
| JP | 09-025241 A | 1/1997 |
| JP | 10-067679 A | 3/1998 |
| SE | 468480 B | 1/1993 |
| SU | 663404 A1 | 5/1979 |
| WO | WO 89/06547 A1 | 7/1989 |
| WO | WO 89/09784 A1 | 10/1989 |
| WO | WO 91/18017 A1 | 11/1991 |
| WO | WO 92/01229 A1 | 1/1992 |
| WO | WO 93/00807 A1 | 1/1993 |
| WO | WO 93/10143 A1 | 5/1993 |
| WO | WO 93/22336 A1 | 11/1993 |
| WO | WO 93/22337 A1 | 11/1993 |
| WO | WO 94/03179 A1 | 2/1994 |
| WO | WO 94/07510 A1 | 4/1994 |
| WO | WO 94/17834 A1 | 8/1994 |
| WO | WO 94/26286 A1 | 11/1994 |
| WO | WO 95/01804 A1 | 1/1995 |
| WO | WO 95/07713 A1 | 3/1995 |
| WO | WO 95/26750 A1 | 10/1995 |
| WO | WO 95/33488 A1 | 12/1995 |
| WO | WO 96/05809 A1 | 2/1996 |
| WO | WO 96/15150 A1 | 5/1996 |
| WO | WO 96/19918 A1 | 7/1996 |
| WO | WO 96/22107 A1 | 7/1996 |
| WO | WO 96/30041 A1 | 10/1996 |
| WO | WO 97/11957 A1 | 4/1997 |
| WO | WO 97/16966 A1 | 5/1997 |
| WO | WO 97/19687 A1 | 6/1997 |
| WO | WO 97/42980 A1 | 11/1997 |
| WO | WO 00/48635 A1 | 8/2000 |
| WO | WO 01/03726 A1 | 1/2001 |
| WO | WO 2005/058283 A2 | 6/2005 |
| WO | WO 2007/074880 A1 | 7/2007 |
| WO | WO 2007/124090 A2 | 11/2007 |
| WO | WO 2010/026186 A1 | 3/2010 |

OTHER PUBLICATIONS

RD 244027, Aug. 10, 1984.
Abdul-Fattah, A.M. et al., "The Effect of Annealing on the Stability of Amorphous Solids: Chemical Stability of Freeze-Dried Moxalactam," *Journal of Pharmaceutical Sciences*, May 2007, vol. 96, No. 5, pp. 1237-1250.
Andersson, L.-O. et al., "Isolation and characterization of human factor VIII: Molecular forms in commercial factor VIII concentrate, cryoprecipitate, and plasma,"*Proc. Natl. Acad. Sci. USA*, May 1986, vol. 83, pp. 2979-2983.
Arakawa, T. et al., "Preferential Interactions of Proteins with Solvent Components in Aqueous Amino Acid Solutions," *Archives of Biochemistry and Biophysics*, Jul. 1, 1983, vol. 224, No. 1, pp. 169-177.
Arakawa, T., "The Stabilization of β-Lactoglobulin by Glycine and NaCl," *Biopolymers*, 1989, vol. 28, pp. 1397-1401.
Arakawa, T. et al., "Protein-Solvent Interactions in Pharmaceutical Formulations," *Pharmaceutical Research*, 1991, vol. 8, No. 3, pp. 285-291.
Austen, D.E.G. and J. K. Smith; "Factro VIII fractionation on aminohezyl sepharose with possible reduction in hepatitis B antigen"; *Throm. Haemostas*; 1982; pp. 46-48; vol. 48, No. 1; Stuttgart.
Austin, D. E. G.; "The chromatographic separation of factor VIII on aminohexyl sepharose"; *British Journal of Haematology*; 1979; pp. 669-674; vol. 43.
Ben-Hur, E. et al.; "Virus inactivation in red cell concentrates by photosensitization with phthalocyanines: protection of red cells but not of vesicular stomatitis virus with a water soluble analogue of vitamin E"; *Transfusion*; 1995; pp. 401-406; vol. 35.
Bhatnagar. B.S. et al., "Study of the Individual Contributions of Ice Formation and Freeze-Concentration on Isothermal Stability of Lactate Dehydrogenase during Freezing," *Journal of Pharmaceutical Sciences*, Feb. 2008, vol. 97, No. 2, pp. 798-814.
Blolmback et al.; "The effect of reducing agents on factor VIII and other coagulation factors"; *Thrombosis Research*; 1978; pp. 1177-1194; vol. 12.

Bohnert, Janice L. and Thomas A. Horbett; Changes in adsorbed fibrinogen and albumin interactions with polymers indicated by decreases in detergent elutability; *Journal of Colloid and Interface Science*; 1986; pp. 363-377; vol. III, No. 2.
Burnouf, T. et al.; "A highly purified factor VIII:c concentrate prepared from cryoprecipitate by ion-exchange chromatography"; *Vox Sang.*; 1991; pp. 8-15; vol. 60.
Carpenter, J.F. et al., "Interactions of Stabilizing Additives With Proteins During Freeze-Thawing and Freeze Drying," *International Symposium on Biological Product Freeze-Drying and Formulation*, Oct. 24-26, Bethesda, MD, 1990, 1992, pp. 225-239.
Carpenter, J.F. et al., "Separation of Freezing- and Drying-Induced Denaturation of Lyophilized Proteins Using Stress-Specific Stabilization," *Archives of Biochemistry and Biophysics*, Jun. 1993, vol. 303, No. 2, pp. 456-464.
Carpenter, J.F. et al., "Lyophilization of Protein Pharmaceuticals," Chapter 4 in *Biotechnology and Biopharmaceutical Manufacturing, Processing, and Preservation*, Avis, K.E. et al., eds., Interpharm Press Inc., Buffalo Grove, IL, 1996, pp. 199-264.
Carpenter, J.F. et al., "Rational Design of Stable Lyophilized Protein Formulations: Some Practical Advice," *Pharmaceutical Research*, 1997, vol. 14, No. 8, pp. 969-975.
Chang, B.S. et al., "Development of an Efficient Single-Step Freeze-Drying Cycle for Protein Formulations," *Pharmaceutical Research*, 1995, vol. 12, No. 6, pp. 831-837.
Chang, B.S. et al., "Development of a Stable Freeze-dried Formulation of Recombinant Human Interleukin-1 Receptor Antagonist," *Pharmaceutical Research*, 1996, vol. 13, No. 2, pp. 243-249.
Chang, B.S. et al., "Surface-Induced Denaturation of Proteins during Freezing and Its Inhibition by Surfactants," *Journal of Pharmaceutical Sciences*, Dec. 1996, vol. 85, No. 12, pp. 1325-1330.
Chang, Byoeng S. and Cynthia S. Randall; "Use of subambient thermal analysis to optimize protein lyophilization"; *Cryobiology*; 1992; pp. 632-656; vol. 29.
Chen, B. et al., "Influence of Calcium Ions of the Structure and Stability of Recombinant Human Deoxyribonuclease I in the Aqueous and Lyophilized States," *Journal of Pharmaceutical Sciences*, Apr. 1999, vol. 88, No. 4, pp. 477-482.
Chen, B. et al., "Influence of Histidine on the Stability and Physical Properties of a Fully Human Antibody in Aqueous and Solid Forms," *Pharmaceutical Research*, Dec. 2003, vol. 20, No. 12, pp. 1952-1960.
Chen, Hao and Al L. Tappel; "Protection of vitamin E, selenium, Trolox C, ascorbic acid, palmitate, acetylcysteine, coenzyme Q0, coenzyme Q10, beta-carotene, canthazanthin, and (+)-catechin against oxidative damage to rat blood and tissues in vivo"; *Free Radical Biology & Medicine*; 1995; pp. 949-953; vol. 18.
Chen, T., "Formulation Concerns of Protein Drugs," *Drug Development and Industrial Pharmacy*, 1992, vol. 18, No. 11 & 12, pp. 1311-1354.
Chin et al.; "Virucidal short wavelength ultraviolet light treatment of plasma and factor VIII concentrate: Protection of proteins by antioxidants"; *Blood*; 1995; pp. 4331-4336; vol. 86, No. 11.
Cleland, J. and R. Langer, eds.; "Formulation and delivery of protein and peptides"; Chapter 1 (Jeffrey L. Cleland) and Chapter 8 (Michael J. Pikal), pp. 1-17 & 120-133, 1994.
Derrick, T.S. et al., "Effect of Metal Cations on the Conformation and Inactivation of Recombinant Human Factor VIII," *Journal of Pharmaceutical Sciences*, Oct. 2004, vol. 93, No. 10, pp. 2549-2557.
Dwight, J. and B. Hendry; "The effects of tert-butyl hydroperoxideon human erythrocyte membrane ion transport and the protective actions of antioxidants"; *Clinica Chimica Acta*; 1996; pp. 167-181; vol. 249.
Edwards, Carol A. et al.; "Tri (n-butyl) phosphate/detergent treatment of licensed therapeutic and experimental blood derivatives"; *Vox Sang.*; 1987; pp. 53-59; vol. 52.
Fatouros et al.; "Recombinant factor VIII SQ: Stability in solution"; Sixteenth ISTH meeting, Jun. 6-12, 1997, Florence.
Fatouros et al.; "Recombinant factor VIII SQ-inactivation kinetics in aqueous solution and the influence of disaccharides and sugar alcohols"; *Pharmaceutical Research*; 1997; pp. 1679-1684; vol. 14, No. 12.

(56) References Cited

OTHER PUBLICATIONS

Fatouros, A. et al., "Recombinant factor VIII SQ—influence of oxygen, metal ions, pH and ionic strength on its stability in aqueous solution," *International Journal of Pharmaceutics*, 1997, vol. 155, pp. 121-131.
Faure et al.; "Improved buffer for the chromatographic separation of factor VIII coagulant"; *Journal of Chromatography*; 1983; pp. 398-391; vol. 257.
Foster, Peter R. et al.; "Studies on the stability of VIII:C during the manufacture of a factor VIII concentrate for clinical use"; *Vox Sang.*; 1988; pp. 81-89; vol. 55.
Franks, F., "Long-Term Stabilization of Biologicals," *Bio-Technology*, Mar. 1994, vol. 12, pp. 253-256.
Gekko, K. et al., "Increased Thermal Stability of Collagen in the Presence of Sugars and Polyols, " *J. Biochem.*, 1983, vol. 94, pp. 199-205.
Gekko, K. et al., "Polyol-induced Stabilization of a Cold-labile Protein," *Agric. Biol. Chem.*, 1991, vol. 55, No. 6, pp. 1663-1664.
Gitschier, J. et al., "Characterization of the human factor VIII gene," *Nature*, Nov. 1984, vol. 312, No. 22, pp. 326-330.
Goulian, M and W. S. Beck; "Stabilization of factor 8 by glycerol"; *Nature*; 1966; pp. 74-75; vol. 211, No. 44.
Hart, H. F. et al.; "Effect of terminal (dry) heat treatment on non-enveloped viruses in coagulation factor concentrates"; *Vox Sang.*; 1994; pp. 345-350; vol. 67.
Hawe, A. et al., "Physico-chemical lyophilization behavior of mannitol, human serum albumin formulations," European Journal of Pharmaceutical Sciences, 2006, vol. 28, pp. 224-232.
Heimberger, Von N. et al.; "Faktor VIII-Konzentrat hochgereinigt und in Losung erhitzt"; *Drug Res.*; 1981; p. 619; vol. 31.
Heller, M. et al., "Manipulation of lyophilization-induced phase separation: implications for pharmaceutical proteins"; 1997; *Biotechnol. Prog.*; pp. 590-596; vol. 13, No. 5.
Her, L-M. et al., "Electrolyte-Induced Changes in Glass Transition Temperatures of Freeze-Concentrated Solutes," *Pharmaceutical Research*, 1995, vol. 12, No. 5, pp. 768-772.
Hollander-Rodriguez, J.C. et al., "Hyperkalemia," *American Family Physician*, Jan. 15, 2006, vol. 73, No. 2, pp. 283-290.
Horowitz, B. et al.; "Inactivation of viruses in labile blood derivatives. II. Physical methods"; *Transfusion*; 1985; pp. 523-527; vol. 25 (Abstract only from Index Medicurs, Medline database).
Horowitz, B. et al.; "Inactivation of lipid-enveloped viruses in labile blood derivatives. II. Physical methods"; *Vox Sang.*; 1988; pp. 14-20; vol. 54.
Jameel, F. et al., "Development of freeze-dried biosynthetic Factor VIII: I. A case study in the optimization of formulation," *Pharmaceutical Development and Technology*, 2009, vol. 14, No. 6, pp. 687-697.
Kappelgaard, A-M. et al., "Liquid Growth Hormone: Preservatives and Buffers," *Hormone Research*, 2004, vol. 62(Suppl 3), pp. 98-103.
Kowolenko, M. et al.; "Preclinical evaluation of an improved formulation of human recombinant FVIII (Kogenate-2): toxicology, pharmacology, pharmacokinetics, and neoantigenicity"; *Thromb. & Haemostatis Supplement*; 1993; p. 509 (Abstract No. PS-2084).
Lam, X.M. et al., "Antioxidants for Prevention of Methionine Oxidation in Recombinant Monoclonal Antibody HER2," *Journal of Pharmaceutical Sciences*, Nov. 1997, vol. 86, No. 11, pp. 1250-1255.
Laursen, T. et al., "Pain Perception after Subcutaneous Injections of Media Containing Different Buffers," *Basic & Clinical Pharmacology & Toxicology*, 2006, vol. 98, pp. 218-221.
Lee, J.C. et al., "The Stabilization of Proteins by Sucrose," *The Journal of Biological Chemistry*, Jul. 25, 1981, vol. 256, No. 14, pp. 7193-7201.
Lueckel, B. et al., "Formulations of Sugars with Amino Acids or Mannitol-Influence of Concetration Ratio on the Properties of the Freeze-Concentrate and the Lyophilizate," *Pharmaceutical Development and Technology*, 1998, vol. 3, No. 3, pp. 325-336.
MacKenzie, A.P. et al., "Non-Equilibrium Freezing Behavior of Aqueous Systems," *Phil. Trans. R. Soc. Lona. B.*, 1977, vol. 278, pp. 167-189.
Manning, Mark C. et al.; "Stability of protein pharmaceuticals"; *Pharmaceutical Research*; 1989; pp. 903-918; vol. 6, No. 11.
Margolis-Nunno, B. et al.; "Virus sterilization in platelet concentrates with psoralen and ultraviolet A light in the presence of quenchers"; *Transfusion*; 1992; pp. 541-547; vol. 32.
McIntosh, R. V. et al.; "A high-yield factor VIII concentrate suitable for advanced heat treatment"; *Thrombosis Haemostasis*; 1987; p. 306; Abstract No. 1119.
McIntosh, Ronald V. and Peter R. Foster; The effect of solution formulation on the stability and surface interactions of factor VIII during plasma fractionation; *Transfus. Sci.*; 1990; pp. 55-66; vol. 11.
Minogue, S.C. et al., "Bacteriostatic Saline Containing Benzyl Alcohol Decreases the Pain Associated with the Injection of Propofol," *Anesth Analg*, 2005, vol. 100, pp. 683-686.
Morganthaler, J. J.; "Chromatography of antihemophilic factor on diaminoalkane- and aminoalkane-derivatized sepharose"; *Throm. Haemostatas*; 1982; pp. 124-127; vol. 47, No. 2; Stuttgart.
Nayar et al.; "Recombinate Kogenate®, formulation development"; *Thromb. & Haemostasis Supplement*; 1993; p. 509 (Abstract No. PS-2081).
Oguchi, Toshio et al.; "Freeze-drying of drug-additive binary systems III. Crystallization of α-cyclodextrin inclusion complex in freezing process"; 1990, *International Journal of Pharmaceutics*, vol. 61, pp. 27-34.
Osterberg et al.; "Developoment of a freezer-dried HAS-free formulation of a new recombinant factor VIII derivative, r-VIII SQ"; ISTH Poster Abstract Book; 1993, p. 1099.
Osterberg, Thomas et al.; "Development of a freeze-dried albumin-free formulation of recombinant factor VIII SQ"; *Pharmaceutical Research*; 1997; pp. 892-898; vol. 14, No. 7.
Over, J., "Methodology of the One-Stage Assay of Factor VIII (VIII:C)," *One-stage Factor VIII assay*, pp. 13-24.
Owen et al.; "Antihemophilic factor: Separation of an active fragment following dissociation by salts or detergents"; *Thrombosis et Diathesis Haemorrhagica*; 1972; pp. 502-515; vol. XXVII, No. 3.
Parti, R. et al., "In vitro stability of recombinant human factor VIII (Recombinate™)," *Haemophilia*, 2000, vol. 6, pp. 513-522.
Pikal, M.J. et al., "The Stability of Insulin in Crystalline and Amorphous Solids: Observation of Greater Stability for the Amorphous Form," *Pharmaceutical Research*, 1997, vol. 14, No. 10, pp. 1379-1387.
Pikal, M.J. et al., "Solid State Chemistry of Proteins: II. The Correlation of Storage Stability of Freeze-Dried Human Growth Hormone (hGH) with Structure and Dynamics in the Glassy Solid," *Journal of Pharmaceutical Sciences*, Dec. 2008, vol. 97, No. 12, pp. 5106-5121.
Plamer, D. S. et al.; "Development of a heat-treated factor VIII/von Williebrand factor concentrate prepared from heparinized plasma"; *Thrombosis and Haemostatis*; 1990; pp. 392-402; vol. 63, No. 3.
Potera, C.; "A sweet way to keep proteins safe"; *Science*; 1998; p. 1973; vol. 281, No. 5384.
Powell, M.F. et al., "Compendium of Excipients for Parenteral Formulations," *PDA Journal of Pharmaceutical Science & Technology*, Sep.-Oct. 1998, vol. 52, No. 5, pp. 238-311.
Remmele, JR., RL. et al., "Interleukin-1 Receptor (IL-1R) Liquid Formulation Development Using Differential Scanning Calorimetry," *Pharmaceutical Research*, 1998, vol. 15, No. 2, pp. 200-208.
Remmele, JR., RL. et al., "Minimization of Recombinant Human Flt3 Ligand Aggregation at the $T_m$ Plateau: A Matter of Thermal Reversibility," *Biochemistry*, 1999, vol. 38, pp. 5241-5247.
Ronzi, E. et al., "Optimisation of a freeze-drying process of high purity Factor VIII and Factor IX concentrates," *Chemical Engineering and Processing*, 2003, vol. 42, pp. 751-757.
Roser, Bruce; "Trehalose drying: A novel replacement for freeze-drying"; *Biopharm*; 1991; pp. 47-53; vol. 4, No. 8.
Roy, S. et al., "Effects of Benzyl Alcohol on Aggregation of Recombinant Human Interleukin-1-Receptor Antagonist in Reconstituted Lyophilized Formulations," *Journal of Pharmaceutical Sciences*, Feb. 2005, vol. 94, No. 2, pp. 382-396.
Rywkin, S. et al.; "Importance of type I and type II mechanisms in the photodynamic inactivation of viruses in blood with aluminum phthalocyanine derivatives"; *Photochemistry and Photobiology*; 1992; pp. 463-469; vol. 56.

(56) References Cited

OTHER PUBLICATIONS

Sugiyama, H. et al.; "Purpurgallin as an antioxidant protector of human erythrocytes against lysis by peroxyl radicals"; *Life Sciences*; 1993; pp. 39-43; vol. 53.

Tandon, Shohba and Paul M. Horowitz; "Detergent-assisted refolding of guanidinium chloride-denatured rhodanese"; *Journal of Biological Chemistry*; 1987; pp. 4486-4491; vol. 262, No. 10.

Tang, X. et al., "Design of Freeze-Drying Processes for Pharmaceuticals: Practical Advice," *Pharmaceutical Research*, Feb. 2004, vol. 21, No. 2, pp. 191-200.

Thompson, A.R., "Structure and Function of the Factor VIII Gene and Protein," *Seminars in Thrombosis and Hemostasis*, 2003, vol. 29, No. 1, pp. 11-22.

Tomita, M. et al., "Sensitized Photooxidation of Histidine and Its Derivatives. Products and Mechanism of the Reaction," *Sensitized Photooxidation of N-BZ-HIS*, Dec. 1969, vol. 8, No. 12, pp. 5149-5160.

UNIPROTKB/SWISS-PROT P00451 (FA8_HUMAN), Mar. 2, 2010, Version 152, 30 pages.

Vehar, G.A., et al., "Structure of human factor VIII," *Nature*, Nov. 1984, vol. 312, No. 22, pp. 337-342.

Wang, D.Q. et al., "Effect of Collapse on the Stability of Freeze-Dried Recombinant Factor VIII and α-Amylase," *American Pharmacists Association J Pharm Sci*, 2004, vol. 93, pp. 1253-1263.

Yin, J. et al., "Effects of Antioxidants on the Hydrogen Peroxide-Mediated Oxidation of Methionine Residues in Granulocyte Colony-Stimulating Factor and Human Parathyroid Hormone Fragment 13-34," *Pharmaceutical Research*, Dec. 2004, vol. 21, No. 12, pp. 2377-2383.

Yoshioka, S. et al., "Usefulness of the Kohlrausch-Williams-Watts Stretched Exponential Function to Describe Protein Aggregation in Lyophilized Formulations and the Temperature Dependence Near the Glass Transition Temperature," *Pharmaceutical Research*, 2001, vol. 18, No. 3, pp. 256-260.

Yu, L. et al., "Existence of a Mannitol Hydrate during Freeze-Drying and Practical Implications," *Journal of Pharmaceutical Sciences*, Feb. 1999, vol. 88, No. 2, pp. 196-198.

\* cited by examiner

ALBUMIN-FREE FACTOR VIII FORMULATIONS

CROSS-REFERENCES TO RELATED APPLICATIONS

This application is a continuation of U.S. application Ser. No. 13/760,900 filed on Feb. 6, 2013, which is a continuation of U.S. application Ser. No. 13/250,789 filed on Sep. 30, 2011 (now U.S. Pat. No. 8,372,800 issued Feb. 12, 2013), which is a continuation of U.S. application Ser. No. 11/764,770 filed Jun. 18, 2007 (now U.S. Pat. No. 8,058,226 issued Nov. 15, 2011), which is a continuation of U.S. application Ser. No. 11/434,634 filed May 15, 2006 (now U.S. Pat. No. 7,247,707 issued Jul. 24, 2007), which is a divisional of U.S. application Ser. No. 10/610,723 filed Jul. 1, 2003 (now U.S. Pat. No. 7,087,723 issued Aug. 8, 2006), which is a continuation of U.S. application Ser. No. 09/507,011 filed Feb. 22, 2000 (now U.S. Pat. No. 6,586,573 issued Jul. 1, 2003), which is a continuation-in-part of U.S. application Ser. No. 09/452,752 filed Dec. 1, 1999 (now abandoned), which is a continuation-in-part of U.S. application Ser. No. 09/255,279 filed Feb. 22, 1999 (now abandoned).

BACKGROUND OF THE INVENTION

Factor VIII is a protein found in blood plasma which acts as a cofactor in the cascade of reactions leading to blood coagulation. A deficiency in the amount of Factor VIII activity in the blood results in the clotting disorder known as hemophilia A, an inherited condition primarily affecting males. Hemophilia A is currently treated with therapeutic preparations of Factor VIII derived from human plasma or manufactured using recombinant DNA technology. Such preparations are administered either in response to a bleeding episode (on-demand therapy) or at frequent, regular intervals to prevent uncontrolled bleeding (prophylaxis).

Factor VIII is known to be relatively unstable in therapeutic preparations. In blood plasma, Factor VIII is usually complexed with another plasma protein, von Willebrand factor (vWF), which is present in plasma in a large molar excess to Factor VIII and is believed to protect Factor VIII from premature degradation. Another circulating plasma protein, albumin, may also play a role in stabilizing Factor VIII in vivo. Currently marketed Factor VIII preparations therefore primarily rely on the use of albumin and/or vWF to stabilize Factor VIII during the manufacturing process and during storage.

The albumin and vWF used in currently marketed Factor VIII preparations is derived from human blood plasma, however, and the use of such material has certain drawbacks. Because a large molar excess of albumin compared to Factor VIII is generally added in order to increase the stability of the Factor VIII in such preparations, it is difficult to characterize the Factor VIII protein itself in these preparations. The addition of human-derived albumin to Factor VIII is also perceived as being a disadvantage with respect to recombinantly-produced Factor VIII preparations. This is because recombinantly-derived Factor VIII preparations, in the absence of such added albumin, would otherwise contain no human-derived proteins, and the theoretical risk of transmitting a virus would be reduced.

Several attempts to formulate Factor VIII without albumin or vWF (or with relatively low levels of these excipients) have been described. For example, U.S. Pat. No. 5,565,427 (EP 508 194) to Freudenberg (assigned to Behringwerke) describes Factor VIII preparations which contain particular combinations of detergent and amino acids, specifically arginine and glycine, in addition to excipients such as sodium chloride and sucrose. The detergent, polysorbate 20 or polysorbate 80, is described as being present in amounts of between 0.001 to 0.5% (v/v), while arginine and glycine are present in amounts of between 0.01 to 1 mol/l. Sucrose is described as being present in amounts of between 0.1 and 10%. Example 2 of this patent asserts that solutions of (1) 0.75% sucrose, 0.4 M glycine, and 0.15M NaCl, and (2) 0.01 M sodium citrate, 0.08 M glycine, 0.016M lysine, 0.0025 M calcium chloride, and 0.4 M sodium chloride were not stable in solution over 16 hours, whereas solutions of (3) 1% sucrose, 0.14 M arginine, 0.1 M sodium chloride and (4) 1% sucrose, 0.4 M glycine, 0.14 M arginine, 0.1 M sodium chloride, and 0.05% Tween 80 exhibited stability.

U.S. Pat. No. 5,763,401 (EP 818 204) to Nayer (assigned to Bayer) also describes a therapeutic Factor VIII formulation without albumin, comprising 15-60 mM sucrose, up to 50 mM NaCl, up to 5 mM calcium chloride, 65-400 mM glycine, and up to 50 mM histidine. The following specific formulations were identified as being stable: (1) 150 mM NaCl, 2.5 mM calcium chloride, and 165 mM mannitol; and (2) 1% sucrose, 30 mM sodium chloride, 2.5 mM calcium chloride, 20 mM histidine, and 290 mM glycine. A formulation containing higher amounts of sugar (10% maltose, 50 mM NaCl, 2.5 mM calcium chloride, and 5 mM histidine) was found to exhibit poor stability in the lyophilized state compared with formulation (2).

U.S. Pat. No. 5,733,873 (EP 627 924) to Osterberg (assigned to Pharmacia & Upjohn) discloses formulations which include between 0.01-1 mg/ml of a surfactant. This patent discloses formulations having the following ranges of excipients: polysorbate 20 or 80 in an amount of at least 0.01 mg/ml, preferably 0.02-1.0 mg/ml; at least 0.1 M NaCl; at least 0.5 mM calcium salt; and at least 1 mM histidine. More particularly, the following specific formulations are disclosed: (1) 14.7-50-65 mM histidine, 0.31-0.6 M NaCl, 4 mM calcium chloride, 0.001-0.02-0.025% polysorbate 80, with or without 0.1% PEG 4000 or 19.9 mM sucrose; and (2) 20 mg/ml mannitol, 2.67 mg/ml histidine, 18 mg/ml NaCl, 3.7 mM calcium chloride, and 0.23 mg/ml polysorbate 80.

Other attempts to use low or high concentrations of sodium chloride have also been described. U.S. Pat. No. 4,877,608 (EP 315 968) to Lee (assigned to Rhone-Poulenc Rorer) teaches formulations with relatively low concentrations of sodium chloride, namely formulations comprising 0.5 mM-15 mM NaCl, 5 mM calcium chloride, 0.2 mM-5 mM histidine, 0.01-10 mM lysine hydrochloride and up to 10% sugar. The "sugar" can be up to 10% maltose, 10% sucrose, or 5% mannitol.

U.S. Pat. No. 5,605,884 (EP 0 314 095) to Lee (assigned to Rhone-Poulenc Rorer) teaches the use of formulations with relatively high concentrations of sodium chloride. These formulations include 0.35 M-1.2 M NaCl, 1.5-40 mM calcium chloride, 1 mM-50 mM histidine, and up to 10% of a "sugar" such as mannitol, sucrose, or maltose. A formulation comprising 0.45 M NaCl, 2.3 mM calcium chloride, and 1.4 mM histidine is exemplified.

International Patent Application WO 96/22107 to Roser (assigned to Quadrant Holdings Cambridge Limited) describes formulations which include the sugar trehalose. These formulations comprise: (1) 0.1 M NaCl, 15 mM calcium chloride, 15 mM histidine, and 1.27 M (48%) trehalose; or (2) 0.011% calcium chloride, 0.12% histidine, 0.002% Tris, 0.002% Tween 80, 0.004% PEG 3350, 7.5% trehalose, and either 0.13% or 1.03% NaCl.

Other therapeutic Factor VIII formulations of the prior art generally include albumin and/or vWF for the purpose of stabilizing Factor VIII and are therefore not relevant to the present invention. For example, U.S. Pat. No. 5,328,694 (EP 511 234) to Schwinn (assigned to Octapharma AG) describes a formulation which includes 100-650 mM disaccharide and 100 mM-1.0 M amino acid. Specifically, the following formulations are disclosed: (1) 0.9 M sucrose, 0.25 M glycine, 0.25 M lysine, and 3 mM calcium chloride; and (2) 0.7 M sucrose, 0.5 M glycine, and 5 mM calcium chloride.

While several attempts have been made to formulate Factor VIII without albumin or vWF, there remains a need for therapeutic Factor VIII formulations which are stable in the absence of albumin or other proteins.

BRIEF SUMMARY OF THE INVENTION

The present invention relates to therapeutic Factor VIII compositions which are stable in the absence of albumin. In particular, the present invention comprises a Factor VIII composition comprising, in addition to Factor VIII: 4% to 10% of a bulking agent selected from the group consisting of mannitol, glycine and alanine; 1% to 4% of a stabilizing agent selected from the group consisting of sucrose, trehalose, raffinose, arginine; 1 mM to 5 mM calcium salt; 100 mM to 300 mM NaCl; and a buffering agent for maintaining a pH of approximately between 6 and 8. This composition can additionally comprise a surfactant such as polysorbate 20, polysorbate 80, Pluronic F68, or Brij 35. When the surfactant is polysorbate 80, it should be present in an amount of less than 0.1%.

The buffer of the Factor VIII compositions according to the present invention is preferably present in a concentration of from 10 mM to 50 mM, and is preferably selected from the group consisting of histidine, Tris, BIS-Tris Propane, PIPES, MOPS, HEPES, MES and ACES. Advantageously, the buffering agent is either histidine or Tris. The Factor VIII composition of the present invention can further comprise an antioxidant.

The Factor VIII compositions of the present invention include both a bulking agent and a stabilizer. The bulking agent can be present in an amount of from about 6% to about 8%, preferably about 8%. The stabilizing agent is preferably present in an amount of about 2%. Sodium chloride is also present in these compositions, preferably in an amount of from 150 to 350 mM, and more preferably in an amount of about 225 mM. The calcium salt of the composition is also preferably calcium chloride, and the composition itself is preferably in lyophilized form.

In another embodiment, the present invention can comprise a Factor VIII composition formulated without adding albumin which includes the following excipients in addition to Factor VIII: 2% to 6% hydroxyethyl starch; 1% to 4% of a stabilizing agent selected from the group consisting of sucrose, trehalose, raffinose, arginine; 1 mM to 5 mM calcium salt; 100 mM to 300 mM NaCl; and a buffering agent for maintaining a pH of approximately between 6 and 8. Preferably, such a composition comprises about 4% hydroxyethyl starch, and the NaCl is present in an amount of 200 mM. The stabilizing agent is also preferably present in an amount of about 2%.

In a further embodiment, the present invention includes a Factor VIII composition, formulated without albumin, comprising: 300 mM to 500 mM NaCl; 1% to 4% of a stabilizing agent selected from the group consisting of sucrose, trehalose, raffinose, arginine; 1 mM to 5 mM calcium salt; and a buffering agent for maintaining a pH of approximately between 6 and 8. Preferably, the NaCl is present in a concentration of about 400 mM.

In yet another embodiment, the present invention comprises a process for lyophilizing an aqueous Factor VIII composition in a container using a lyophilizer, wherein the process comprises an initial freezing step, and the initial freezing step further comprises the steps of: (a) lowering the temperature of the lyophilizer chamber to at least about −45° C.; (b) raising the temperature of the chamber to between about −15° C. and −25° C.; and subsequently (c) lowering the temperature of the chamber to at least about −45° C. In this process, the temperature of the chamber is preferably lowered or raised at a rate of between about 0.5° C. and about 1.0° C. per minute. In step (a), the temperature is preferably maintained for about 1 hour, and is lowered to about −55° C. In step (b) the temperature is preferably maintained be −15° C. and −25° C. for between 1 and 3 hours, and more preferably is at −22° C., and the temperature in step (c) is preferably maintained for about 1 hour. The Factor VIII composition used in this process preferably comprises between 4% and 10% of an agent selected from the group consisting of mannitol, glycine and alanine, and also preferably comprises between 1% and 4% of an agent selected from the group consisting of sucrose, trehalose, raffinose, and arginine. In addition, the Factor VIII composition used in this process also preferably comprises between 100 mM and 300 mM NaCl.

DETAILED DESCRIPTION OF THE INVENTION

Definitions

As used herein, the terms below and variations thereof shall be defined as follows, unless otherwise indicated:

Factor VIII—The Factor VIII molecule exists naturally and in therapeutic preparations as a heterogeneous distribution of polypeptides arising from a single gene product (see, e.g., Andersson et al., Proc. Natl. Acad. Sci. USA, 83, 2979-2983, May 1986). The term "Factor VIII" as used herein refers to all such polypeptides, whether derived from blood plasma or produced through the use of recombinant DNA techniques. Commercially available examples of therapeutic preparations containing Factor VIII include those sold under the trade names of HEMOFIL M and RECOMBINATE (available from Baxter Healthcare Corporation, Deerfield, Ill., U.S.A.). Other preparations currently in development comprise primarily a single subpopulation of Factor VIII molecules which lack the B domain portion of the molecule.

International Unit, IU—International Unit, or IU, is a unit of measurement of the blood coagulation activity (potency) of Factor VIII as measured by a standard assay, such as one of the following:

One stage assay. One stage assays are known to the art, such as that described in Lee, Martin L, et al., *An Effect of Predilution on Potency Assays of Factor VIII Concentrates*, Thrombosis Research (Pergamon Press Ltd.) 30, 511-519 (1983).

Chromogenic assay. Chromogenic assays may be purchased commercially, such as the Coatest Factor VIII, available from Chromogenix AB, Molndal, Sweden.

Anneal—The term anneal shall be used to indicate a step in the lyophilization process of a pharmaceutical preparation undergoing lyophilization, prior to the freeze-drying of the preparation, in which the temperature of the preparation is raised from a lower temperature to a higher temperature and then cooled again after a period of time.

Bulking Agent—For the purposes of this application, bulking agents are those chemical entities which provide structure to the "cake" or residual solid mass of a pharmaceutical preparation after it has been lyophilized and which protect it against collapse. A crystallizable bulking agent shall mean a bulking agent as described herein which can be crystallized during lyophilization, other than sodium chloride. HES is not included in this group of crystallizable bulking agents.

Freeze-drying, freezing, lyophilizing—"Freeze-drying," unless otherwise indicated by the context in which it appears, shall be used to denote the portion of a lyophilization process in which the temperature of a pharmaceutical preparation is raised in order to drive water out of the preparation. The "freezing" steps of a lyophilization process are those steps which occur prior to the freeze-drying stage. "Lyophilizing," unless otherwise indicated, shall refer to the entire process of lyophilization, including both the freezing steps and the freeze-drying steps.

Unless otherwise noted, percentage terms express weight/volume percentages and temperatures are in the Celsius scale.

Formulation Components

The Factor VIII compositions of the present invention include bulking agents, stabilizing agents, buffering agents, sodium chloride, calcium salts, and, advantageously, other excipients. These excipients have been chosen in order to maximize the stability of Factor VIII in lyophilized preparations. However, the Factor VIII compositions of the present invention exhibit stability in the liquid state as well.

The bulking agents used in the present formulations, which form the crystalline portion of the lyophilized product (except in the case of HES), are selected from the group consisting of mannitol, glycine, alanine, and hydroxyethyl starch (HES). Mannitol, glycine, or alanine are present in an amount of 4-10%, preferably 6-9%, and more preferably about 8%. When HES is used as a bulking agent, it is present in an amount of 2-6%, preferably 3-5%, and more preferably about 4%.

The stabilizing agents used in the formulations of the present invention are selected from the group consisting of sucrose, trehalose, raffinose, and arginine. These agents are present in the formulations of the present invention in an amount of between 1-4%, preferably 2-3%, more preferably about 2%. Sorbitol and glycerol were evaluated as possible stabilizers but were found to be poor stabilizers in the present formulations.

Sodium chloride is included in the present formulations in an amount of 100-300 mM, preferably 150-250 mM, and most preferably about 225 mM. In one embodiment of the present invention, sodium chloride itself can be used without any of the aforementioned bulking agents, in which case it would be included in the formulation in an amount of between 300 mM and 500 mM NaCl, preferably 350 to 450 mM NaCl, and more preferably about 400 mM NaCl.

In addition, buffers are present in these formulations, because it is believed that the Factor VIII molecule can be adversely affected by pH shifts during lyophilization. The pH should preferably be maintained in the range of between 6 and 8 during lyophilization, and more preferably at a pH of about 7. The buffering agent can be any physiologically acceptable chemical entity or combination of chemical entities which have the capacity to act as buffers, including histidine, Tris, BIS-Tris Propane, PIPES, MOPS, HEPES, MES and ACES. The full chemical designations of these buffering agents is listed in Table 1 below. Typically, the buffering agent is included in a concentration of 10-50 mM. When histidine is added to the formulations, concentrations of over 20 mM and preferably about 25 mM are used, alone or in combination with other buffers such as Tris. Histidine is especially preferred for use in the compositions of the present invention, as described in greater detail below.

TABLE 1

| Buffering Agents | |
| --- | --- |
| Tris | tris-(hydroxymethyl)-aminomethane |
| BIS-Tris Propane | 1,3-bis-[tris-(hydroxy-methyl)methylamino]-propane |
| PIPES | piperazine-N,N'-bis-(2-ethanesulfonic acid) |
| MOPS | 3-{N-morpholino} propanesulfonic acid |
| HEPES | N-2-hydroxyethyl-piperazine-N'-2-ethanesulfonic acid |
| MES | 2-(N-morpholino) ethanesulfonic acid |
| ACES | N-2-acetamido-2-aminoethanesulfonic acid |

In order to preserve the activity of Factor VIII, it is important that the formulations of the present invention also include calcium or another divalent cation able to interact with Factor VIII and maintain its activity, presumably by maintaining the association of the heavy and light chains of Factor VIII. Between 1 mM and 5 mM of a calcium salt can be used, more preferably 3-4 mM, and most preferably about 4 mM. The calcium salt is preferably calcium chloride, but can also be other calcium salts such as calcium gluconate, calcium glubionate, or calcium gluceptate.

The Factor VIII compositions of the present invention also preferably include a surfactant, preferably in an amount of 0.1% or less, and more preferably in an amount of about 0.03%. The surfactant can, for example, be chosen from the group consisting of polysorbate 20, polysorbate 80, pluronic polyols, and Brij 35 (polyoxyethylene 23 lauryl ether). Several grades of pluronic polyols (sold under the trade name Pluronic, manufactured by the BASF Wyandotte Corporation) are available. These polyols, of diversified molecular weight (from 1,000 to over 16,000) and physicochemical properties have been used as surfactants. Pluronic F-38, of a molecular weight of 5,000 and Pluronic F-68, molecular weight 9,000, both contain (by weight) 80 percent hydrophilic polyoxyethylene groups and 20 percent hydrophobic polyoxypropylene groups. Tween-80, a commercial polysorbate, however, is preferred in the present formulations, in particular vegetable-derived Tween-80.

The Factor VIII formulations of the present invention also preferably include an antioxidant. The addition of antioxidants to the lyophilized formulations of the invention has been found to improve the stability of these formulations, and thus extend their shelf lives. The antioxidants used must be compatible for use with a pharmaceutical preparation, and in addition are preferably water soluble. When adding antioxidants to a formulation, it is preferable to add such antioxidants as late in the process prior to lyophilization as possible, in order to avoid spontaneous oxidation of the antioxidant. Table 2 below lists suitable antioxidants, which are available commercially through companies such as Calbiochem and Sigma.

TABLE 2

| Antioxidants |
| --- |
| N-Acetyl-L-Cysteine/Homocysteine |
| Glutathione |
| 6-hydroxy-2,5,7,8-tetramethylchroman-2-carboxylic acid (Trolox) |
| Lipoic acid |
| Methionine |
| Sodium Thiosulfate |
| Platinum |
| Glycine-glycine-histidine (tripeptide) |
| Butylatedhydroxytoluene (BHT) |

Of the foregoing antioxidants, glutathione is preferred. Concentrations in the range of about 0.05 mg/ml to more than 1.0 mg/ml have all been found to enhance the stability of Factor VIII compositions, and it is believed that higher concentrations would also be useful (up to the point of any toxic effects or adverse manufacturing effects, such as a depression of the glass transition temperature of the lyophilized product).

It has been found in particular that the combination of histidine and glutathione produces synergistically beneficial effects on the stability of Factor VIII compositions. Histidine, while acting as a buffer, can also act as a metal chelator. To the extent that Factor VIII inactivation is caused by metal-induced oxidation, histidine can therefore act to stabilize Factor VIII by binding such oxidizing metal ions. It is believed that by binding these metals, the glutathione (or indeed any other antioxidant present) is thereby able to provide further antioxidative protection, since the oxidative effect of the metal ions bound by the histidine has been contained.

Other chelating agents might also be used in the compositions of the present invention. Such agents should preferably bind metals such as copper and iron with greater affinity than calcium, if a calcium salt is being used in the composition. One such chelator is deferoxamine, a chelating agent that facilitates the removal of Al++ and iron. Deferoxamine Mesylate, C25H48N6O8*CH4O3S, can be obtained from Sigma (Sigma Prod. No. D9533). It is an aluminum and iron(II) chelator which chelates iron (as a 1:1 chelate complex) only in the +3 oxidation state, not +2 oxidation state, and can also bind manganese ion and other metals. Deferoxamine can be used advantageously in an amount of 0.25 mg/l.

The Factor VIII used in the present formulations can be either highly purified human plasma-derived Factor VIII or more preferably can be recombinantly produced Factor VIII. Recombinant Factor VIII can be produced by Chinese hamster ovary (CHO) cells transfected with a vector carrying a DNA sequence coding for the Factor VIII molecule. Methods for creating such transfected CHO cells are described, inter alia, in U.S. Pat. No. 4,757,006 to Toole, Jr., though alternative methods are also known to the art (see, e.g., U.S. Pat. No. 4,868,112, also to Toole, Jr., and PCT International Application WO-A-91/09122). The methods used to culture such CHO cells to produce Factor VIII are also known to the art, for example in European Patent Application No. 0 362 218 to Genetics Institute, entitled "Improved method for producing Factor VIII:C-type proteins." Recombinant Factor VIII can, however, also be produced in other cell lines, such as baby hamster kidney (BHK) cells. The Factor VIII molecule itself, if recombinantly produced, can be either full-length Factor VIII or a deletion derivative thereof, such as a B domain-deleted Factor VIII molecule.

While the Factor VIII compositions described in this application can be lyophilized and reconstituted in the indicated concentrations, one of skill in the art will understand that these preparations can also be reconstituted in more dilute form. For example, a preparation according the present invention which is lyophilized and/or normally reconstituted in 2 ml of solution can also be reconstituted in a larger volume of diluent, such as 5 ml. This is particularly appropriate when the Factor VIII preparation is being injected into a patient immediately, since in this case the Factor VIII is less likely to lose activity, which may occur more rapidly in more dilute solutions of Factor VIII.

Formulation and Lyophilization Development

In order to achieve maximal stability, the Factor VIII compositions of the present invention are preferably lyophilized. During lyophilization, Factor VIII is converted from being in an aqueous phase to being in an amorphous solid phase, which is thought to protect the protein from chemical and/or conformational instability. The lyophilized preparation not only contains an amorphous phase, but also includes a component which crystallizes during lyophilization. This is thought to allow the rapid lyophilization of the Factor VIII composition and the formation of a more elegant cake (that is, a cake with minimal shrinkage from the sides of the container in which it was lyophilized). In the formulations of the present invention, the stabilizing agents have been selected to exist primarily in an amorphous phase of the lyophilized product, while the bulking agents (except HES) have been selected to crystallize during freezing.

Both the Factor VIII and the stabilizer are preferably dispersed in the amorphous phase of the lyophilized cake. The mass of the stabilizer is also preferably large compared to the other excipients in the amorphous form. In addition, the apparent glass transition temperature ($T_g'$) of the amorphous phase is preferably relatively high during freeze-drying, and the glass transition temperature (Tg) of the solid is likewise preferably high during storage. Crystallization of sodium chloride in the product was found to be desirable, since amorphous sodium chloride will depress the $T_g'$ of the amorphous phase.

In order to avoid the collapse of the cake of a particular composition, primary drying is preferably carried out at a product temperature below the apparent glass transition temperature of the freeze concentrate. An increase in drying time may also be required to offset a decrease in $T_g$. Further information on lyophilization may be found in Carpenter, J. F. and Chang, B. S., *Lyophilization of Protein Pharmaceuticals*, Biotechnology and Biopharmaceutical Manufacturing, Processing and Preservation, K. E. Avis and V. L. Wu, eds. (Buffalo Grove, Ill.: Interpharm Press, Inc.), pp. 199-264 (1996).

EXAMPLE 1

The effects of the concentration of Factor VIII and of the addition of a stabilizer on the recovery of Factor VIII were investigated in several studies. These studies were performed using mannitol as a model bulking agent and sucrose as a model stabilizer. The three sample formulations described in Table 3 below were used in these studies. All formulations used in these studies included 10 mM Tris, 200 mM NaCl, 8% mannitol, 4 mM $CaCl_2$, and 0.02% Tween-80 and were conducted at pH 7.0.

TABLE 3

| Sample I.D. | Initial Factor VIII (IU/ml) | Sucrose % |
| --- | --- | --- |
| IA | 600 | — |
| IB | 60 | — |
| IC | 60 | 2 |

These samples were lyophilized using the freeze-drying cycle shown in Table 4 below in order to maintain a product temperature below the apparent glass transition temperature ($T_g'$). Differential scanning calorimetric (DSC) studies indicated the presence of a transition at approximately −40° C. in the mannitol formulations. In order to maintain a product temperature below this value, the shelf temperature was set to −32° C. during primary drying. Primary drying under these conditions was performed for about 55 hours, with a total cycle time of about 80 hours.

TABLE 4

| Freezing/Processing Method | Description |
|---|---|
| I (Freezing) | Cool to +5° C.; Cool to −5° C. at 1° C./minute, hold for 20 minutes; Cool to −20 ± 5° C. at 1° C./minute, hold for 1 hour (up to 3 hours); Cool to −45° C. at 0.5° C./minute, hold for 1 hour. |
| II | Freeze per method I Hold at −35° C. for 48 hours. |
| III | Freeze per method I Hold at −35° C. for 48 hours; Hold at −20° C. for 48 hours. |
| IV (Freeze-drying) | Shelf −32° C. during primary drying for about 55 hours (up to 100 hours); Product < −40° C. during primary drying; Ramp from −32° C. to +40° C. at 0.2° C./minute; Shelf +40° C. during secondary drying for 3 hours. |

The Factor VIII activity of these samples, as determined by the one-stage clotting assay, was compared against a control held at −45° C. The assay results are shown in Table 5 below.

TABLE 5

| | % Loss in Factor VIII Activity During Each Step | | |
|---|---|---|---|
| Processing Method | Formulation IA (600 IU/ml) | Formulation IB (60 IU/ml) | Formulation IC (60 IU/ml, 2% Sucrose) |
| I | 6.7 | 37.5 | 41.7 |
| II | 2.0 | 9.3 | 3.9 |
| III | 7.3 | 11.6 | 5.0 |
| IV (Lyophilization) | 20.0 | 24.2 | 18.3 |

These results indicate that protein concentration has an effect on the recovery of Factor VIII during freezing. Formulations containing 60 IU/ml lost approximately 37%-42% of the initial Factor VIII activity during the freezing step, while 6.7% of Factor VIII activity was lost for the formulation containing 600 IU/ml. These results indicate that a higher protein concentration has a protective effect during freezing. Although sucrose provided some protection to the Factor VIII during the intermediate temperature holds as well as during freeze-drying, it failed to protect the protein during the initial freezing step.

EXAMPLE 2

Following the development of the lyophilization process outlined in Example 1, further optimization of this process was undertaken. It has been found that a lyophilized composition having a higher glass transition temperature, (and, theoretically, better Factor VIII stability) can be produced by: (1) lowering the freezing temperature initially to −45° C. or lower (such as down to about −50° C. or −55° C.); (2) raising the temperature to −20° C. or −22° C. (±5° C.); and then (3) lowering the temperature again to −45° C. or lower. The temperature is lowered or raised, as the case may be, at a rate of between about 0.5° C. and about 1.0° C. per minute. Once the desired temperature is reached, the composition is held at that temperature for between 1 and 3 hours. This improved freezing cycle is shown in Table 6 below.

TABLE 6

| Freezing Method | Description |
|---|---|
| I | Cool to +5° C.; Cool to −5° C. at 0.5-1° C./minute, hold for 20 minutes; Cool to between −55° C. and −45° C. at 0.5-1° C./minute, hold for about 1 hour; Warm to −22° C. (±5° C.) at 0.5-1° C./minute, hold for 1 to 3 hours; Cool to −45° C. at 0.5-1° C./minute, hold for about 1 hour. |

Unless otherwise indicated, the temperatures referred to in this example and in other examples refer to the shelf temperature of the lyophilizer and not to the temperature of the product per se. Following the improved freezing cycle, the remainder of the lyophilization process can be conducted as outlined in Example 1 above, or otherwise as described further herein or as determined by one of skill in the art.

This improved lyophilization process was found to be useful for formulations which include glycine as the bulking agent as well as those which use mannitol. It is further believed to have applicability to formulations which make use of the other bulking agents of the present invention as well.

EXAMPLE 3

It is believed that in order to produce a freeze-dried product with acceptable cake appearance and glass transition temperature, the bulking agent of lyophilized pharmaceutical preparations which contain sodium chloride, such as glycine or mannitol, may need to be crystallized. The following improved lyophilization process for crystallizable bulking agents was therefore developed.

TABLE 7a

| Freezing Steps | | |
|---|---|---|
| Process Step | Temperature | Duration of Step |
| Initial freezing | −40° C. or less | 1 hour |
| First annealing | between −23° C. and −27° C. | 3 hours |
| Second freezing | −55° C. | 1 hour |
| Second annealing | −36° C. | 4 hours |
| Third freezing | −50° C. | 1 hour |

TABLE 7b

| Freeze-Drying Steps | | |
|---|---|---|
| Process Step | Temperature | Duration of Step |
| Primary Drying | −35° C. | up to 100 hours |
| Secondary Drying: First step | 40° C. | 3 hours |
| Secondary Drying: Second step | 45° C. | 3 hours |
| Secondary Drying: Third step | 50° C. | 3 hours |

In the freezing steps, changes in the temperatures occurred at a rate of between about 0.5° C./minute and 1° C./minute. It is believed that steps of longer duration would also be effective.

Prior to the first freezing step, the temperature is brought to between about 2° C. and 8° C. for about one hour for the purpose of bringing all the vials to approximately the same temperature. After this the lyophilizer is cooled to −5° C. The first freezing step should be performed at a temperature less than −30° C., preferably below −35° C., and more preferably at about −40° C. Following this, the first annealing step should occur at a temperature of between −30° C. and −19° C., more preferably either between about −25° C. and −28° C. (if glycine is the bulking agent) or between −21° C. and −24° C. (if mannitol is the bulking agent), with the temperatures of −23° C. and −26° C. being most preferred, at which temperatures it is believed that the crystallizable bulking agents crystallize, at least in part. However, the lower range around −27° C. is not recommended for formulations containing mannitol and arginine. This step is preferably carried out for about 3 hours.

Following the first annealing step, the temperature is lowered, preferably to less than about −50° C. and more preferably to less than −55° C., for about 1 hour. It is believed that the sodium chloride in the preparation nucleates at this time.

During the second annealing step, the temperature of the pharmaceutical preparation is raised to between about −30° C. and −39° C., and preferably to about −33° C. for mannitol-containing compositions and −36° C. for glycine-containing compositions. It is believed that NaCl crystal growth occurs at this time, at least in part. This step is preferably conducted for about 4 hours. Following this, the temperature of the lyophilizer is reduced to about −50° C., preferably for about 1 hour in order to reduce the temperature of the preparation.

In the freeze-drying steps which follow, changes in temperature occurred at a rate of between about 0.1° C./minute and 0.5° C./minute. After reducing the pressure in the lyophilizer to about 65 mTorr, the temperature is raised to between about −32° C. and −35° C. for primary drying. Ice crystals in the preparation will sublimate at this temperature. This step is performed for up to about 100 hours, or until most of the ice has been sublimated from the preparation. The point at which most of the ice has sublimated can be determined, for example, using a dewpoint sensor, which indicates the end of the sublimation of ice when the readings decrease (the point of inflection).

Following primary drying, the temperature is raised to +40° C., preferably at a rate of 0.2° C./minute, to initiate secondary drying to remove further water from the preparation. This temperature is preferably maintained for about three hours. Second and third secondary drying steps follow this first step, where the temperature is raised to about +45° C. for about three hours and then to about +50° C. for three more hours in order to reduce the moisture in the lyophilized cake to less than 2% (w/w).

EXAMPLE 4

Further studies were performed to examine specifically the effect of histidine on lyophilized Factor VIII compositions containing glycine or mannitol as bulking agents. Non-reversing heat flow (Modulated DSC, mDSC) was used to detect the crystallization of these bulking agents during cooling. Both the temperature of crystallization and the total heat of crystallization were determined from the crystallization exotherm. The appearance of the NaCl eutectic melt endotherm during warming was used to detect NaCl crystallization. In mDSC, the extent of crystallization was determined as the ratio of the enthalpy of melting of the formulation to the enthalpy of melting of pure NaCl solution by using the total heat flow signal. In addition, X-ray diffraction analyses were performed in order to determine the extent of crystallization in the lyophilized formulations.

While histidine concentrations less than 20 mM did not significantly impact the crystallization of glycine, 50 mM histidine reduced the extent of glycine crystallization. Well-defined NaCl crystallization exotherms were not observed during cooling of formulations containing glycine. However, eutectic melting endotherms during heating indicated that NaCl was crystallized (>50%) after cooling lower than −50° C. and annealing at −30° C., −35° C. and −40° C. The inclusion of 50 mM histidine in the glycine-containing formulation retarded NaCl crystallization. Consequently, the annealing time was increased 3-fold for such formulations in order to achieve an equivalent crystallinity.

However, the effect of 20 mM histidine on the crystallization of NaCl in the glycine-containing formulations was minimal. In freeze-drying studies, collapse of the lyophilized cake was observed visually in glycine-containing formulations containing 50 mM histidine. X-ray powder diffraction data indicated a decrease in the crystallinity of NaCl in samples containing histidine. In mannitol-containing formulations, typically 83%-90% of the sodium chloride crystallized during cooling between −40° C. and −50° C. without the need for annealing. While inclusion of 20 mM histidine to the formulation suppressed NaCl crystallization during cooling, annealing resulted in approximately 40% crystallization of the NaCl.

Therefore, in formulations containing a crystallizable bulking agent, such as glycine or mannitol, and NaCl, the inclusion of histidine may decrease the extent of crystallization of NaCl. Although this could in some cases lead to the collapse of the cake which is formed during lyophilization, the use of relatively lower concentrations of histidine in such formulations can mitigate this effect. Nonetheless, acceptable cakes have been formed with concentrations of histidine of 35 mM and 50 mM. Histidine may also be preferable to HEPES as a buffer in mannitol- and glycine-based formulations, as the use of HEPES has been observed to lower the Tg' to a greater extent than a similar amount of histidine.

EXAMPLE 5

The physical characteristics of a number of potential Factor VIII formulations, including seven candidate stabilizers and five bulking agents, were evaluated in another study. In addition to a bulking agent and stabilizer, all formulations listed in Table 8 below (except for formulation 11) contained 10 mM TrisHCl, 200 mM NaCl, 0.02% Tween-80, 4 mM $CaCl_2$ and were at pH 7.0. Formulation 11 contained 10 mM TrisHCl, 0.02% Tween-80, and 4 mM $CaCl_2$, also at pH 7.0. All pH measurements were performed at ambient temperature.

TABLE 8

| Sample I.D. | Bulking Agent | Protein Stabilizer |
|---|---|---|
| 1 | 8% Mannitol | 2% Sucrose |
| 2 | 8% Mannitol | 2% Trehalose |
| 3 | 8% Mannitol | 2% Raffinose |
| 4 | 8% Mannitol | 2% Arginine |
| 5 | 8% Mannitol | 2% Lysine |
| 6 | 8% Mannitol | 2% Sorbitol |
| 7 | 8% Mannitol | 2% Glycerol |
| 8 | 4% Hydroxyethyl Starch | 2% Sucrose |
| 9 | 8% Glycine | 2% Sucrose |
| 10 | 8% Glycine | 2% Trehalose |
| 11 | 400 mM NaCl | 2% Sucrose |
| 12 | 8% Alanine | 2% Sucrose |

Collapse temperature measurements by freeze-dry microscopy and thermal transition measurements by DSC were used to predict freeze-drying behavior. DSC, X-ray powder diffraction and polarized light microscopy were also used to determine the crystallinity of the lyophilized samples. The reconstitution time and the appearance of the samples were also evaluated. The results of all of these measurements are summarized in Table 9 below.

TABLE 9

| Sample I.D. | $T_{pc}$ (°C.) | $T_c$ (°C.) | $T_g$ (°C.) | Reconstitution (seconds) | Water Content (%) | Appearance |
|---|---|---|---|---|---|---|
| 1 | −14 | −10 | 54 | 64 | n/c | Elegant |
| 2 | −20 | −15 | 53 | 62 | 1.4 | Top partially collapsed |
| 3 | −15 | −10 | 54 | 77 | 1.7 | Elegant |
| 4 | — | — | — | — | — | Partial collapse |
| 5 | — | — | — | — | — | Collapsed |
| 6 | n/c | n/c | <10° C.* | 63 | 0.6 | Elegant |
| 7 | — | — | <10° C.* | — | — | Elegant |
| 8 | — | — | 86 | 49 | 0.7 | Elegant but shrunk from sides |
| 9 | — | — | 54 | 22 | 0.8 | Elegant |
| 10 | — | — | 63 | 18 | — | Elegant |
| 11 | — | — | 66 | 11 | 0.4 | Elegant (layer on bottom) |
| 12 | — | — | — | 57 | 0.5 | Elegant |

*Sorbitol and Glycerol have glass transitions at <10° C. The DSC scan range did not include temperatures in this range.
n/c = not clear
$T_{pc}$ = Temperature at which partial collapse occurs in the freeze-dry microscope
$T_c$ = Temperature at which total collapse occurs in the freeze-dry microscope
$T_g$ = Glass transition temperature With the exception of mannitol:lysine, all of the formulations appeared to have adequate physical appearance. Lysine interfered with the crystallization of both mannitol and glycine, which caused a depression in the glass transition temperature and a collapse of the lyophilized cake.

EXAMPLE 6

The Factor VIII compositions described in Table 8 above were placed in storage at −70° C., 25° C., 40° C., and 50° C. for varying lengths of time in order to evaluate their stability. Factor VIII activity levels were evaluated after 2 weeks, 1 month, 2 months, and 3 months, and the results are summarized in Table 10 below. Two of the samples, one employing mannitol as the bulking agent and sorbitol as the stabilizer, and the other employing mannitol as the bulking agent and glycerol as the stabilizer, exhibited poor stability. The remaining formulations all exhibited the ability to stabilize Factor VIII.

TABLE 10

| Formulation Description | Temperature (° C.) | % of initial at month | | | | |
|---|---|---|---|---|---|---|
| | | 0 | 0.5 | 1 | 2 | 3 |
| Glycine:Sucrose | −70 | 100.00 | 97.43 | 101.71 | 99.89 | 97.97 |
| | 25 | 100.00 | | | | 85.44 |
| | 40 | 100.00 | | 79.87 | 71.52 | 63.06 |
| | 50 | 100.00 | 76.34 | 67.99 | 52.14 | 47.64 |
| Glycine:Trehalose | −70 | 100.00 | 89.22 | 96.00 | 95.90 | 94.64 |
| | 25 | 100.00 | | | | 83.17 |
| | 40 | 100.00 | | 79.93 | 72.42 | 68.03 |
| | 50 | 100.00 | 80.97 | 64.28 | 57.60 | 50.92 |
| Mannitol:Trehalose | −70 | 100.00 | 91.32 | 97.72 | 96.10 | 98.26 |
| | 25 | 100.00 | | | | 85.79 |
| | 40 | 100.00 | | 82.54 | 70.72 | 59.44 |
| | 50 | 100.00 | 66.16 | 65.51 | 48.81 | 52.06 |
| Mannitol:Sucrose | −70 | 100.00 | 100.45 | 100.56 | 105.47 | 99.22 |
| | 25 | 100.00 | | | | 87.04 |
| | 40 | 100.00 | | 85.59 | 80.78 | 55.42 |
| | 50 | 100.00 | 81.68 | 75.53 | 57.88 | 43.46 |
| Mannitol:Arginine | −70 | 100.00 | 102.26 | 105.53 | 103.72 | 105.08 |
| | 25 | 100.00 | | | | 95.15 |
| | 40 | 100.00 | | 91.53 | 80.93 | 69.19 |
| | 50 | 100.00 | 82.28 | 68.06 | 56.32 | 45.94 |
| Mannitol:Raffinose | −70 | 100.00 | 93.88 | 98.41 | 100.68 | 103.62 |
| | 25 | 100.00 | | | | 83.13 |
| | 40 | 100.00 | | 81.09 | 73.61 | 67.16 |
| | 50 | 100.00 | 71.69 | 68.52 | 54.25 | 47.11 |
| Mannitol:Glycerol | −70 | | | | | |
| | 25 | | | | | |
| | 40 | | | | | |
| | 50 | | | | | |
| Mannitol:Sorbitol | −70 | 100.00 | 104.06 | | | |
| | 25 | 100.00 | | | | |
| | 40 | 100.00 | | | | |
| | 50 | 100.00 | 32.73 | | | |
| HES:Sucrose | −70 | 100.00 | 102.74 | 103.03 | 100.90 | |
| | 25 | 100.00 | | | | |
| | 40 | 100.00 | | 76.89 | 77.47 | |
| | 50 | 100.00 | 71.47 | 67.40 | 30.02 | |
| NaCl:Sucrose | −70 | 100.00 | 88.54 | 88.44 | 95.58 | |
| | 25 | 100.00 | | | | |
| | 40 | 100.00 | | 71.56 | 58.30 | |
| | 50 | 100.00 | 52.71 | 37.90 | 30.34 | |
| Alanine:Sucrose | −70 | 100.00 | 109.78 | 109.67 | 108.96 | |
| | 25 | 100.00 | | | | |
| | 40 | 100.00 | | 92.99 | 73.03 | |
| | 50 | 100.00 | 83.25 | 74.91 | 57.65 | |

TABLE 10-continued

| Formulation Description | Temperature (° C.) | % of initial at month | | | | |
|---|---|---|---|---|---|---|
| | | 0 | 0.5 | 1 | 2 | 3 |
| Glycine:Raffinose | −70 | 100.00 | 111.57 | 114.51 | 105.25 | |
| | 25 | 100.00 | | | | |
| | 40 | 100.00 | | 89.20 | 82.10 | |
| | 50 | 100.00 | 93.21 | 72.22 | 53.24 | |

EXAMPLE 7

Based on the information developed during the studies described in Examples 5 and 6, it was decided that candidate formulations having the excipients shown in Table 11 below would be further developed.

TABLE 11

| Excipient | Concentration |
|---|---|
| mannitol or glycine | 6-9% |
| arginine or trehalose | 1-3% |
| tween 80 | 0.005-0.04% |
| NaCl | 200-250 mM |
| CaCl2 | 3-5 mM |
| TRIS | 20-30 mM |
| histidine or HEPES | 10-50 mM |
| glutathione | 0.15-0.25 mg/ml |

Based on these parameters, the following specific formulations were developed:

TABLE 12

| Formulation #1 | Formulation #2 | Formulation #3 |
|---|---|---|
| 10 mM HEPES | 10 mM HEPES | 10 mM HEPES |
| 20 mM Tris | 20 mM Tris | 20 mM Tris |
| 225 mM NaCl | 225 mM NaCl | 225 mM NaCl |
| 0.03% (v/v) Tween-80 | 0.03% (v/v) Tween-80 | 0.03% (v/v) Tween-80 |
| 8% (w/v) mannitol | 8% (w/v) glycine | 8% (w/v) mannitol |
| 2% (w/v) trehalose | 2% (w/v) trehalose | 2% (w/v) arginine |
| 0.2 mg/ml reduced glutathione | 0.2 mg/ml reduced glutathione | 0.2 mg/ml reduced glutathione |
| 4 mM CaCl$_2$ | 4 mM CaCl$_2$ | 4 mM CaCl$_2$ |

| Formulation #4 | Formulation #5 |
|---|---|
| 25 mM histidine | 25 mM histidine |
| 20 mM Tris | 20 mM Tris |
| 225 mM NaCl | 225 mM NaCl |

TABLE 12-continued

| | |
|---|---|
| 0.03% (v/v) Tween-80 | 0.03% (v/v) Tween-80 |
| 8% (w/v) mannitol | 8% (w/v) glycine |
| 2% (w/v) trehalose | 2% (w/v) trehalose |
| 0.2 mg/ml reduced glutathione | 0.2 mg/ml reduced glutathione |
| 4 mM CaCl$_2$ | 4 mM CaCl$_2$ |

What is claimed is:

1. A liquid Factor VIII composition formulated without adding albumin to said composition, said composition comprising the following formulation excipients in addition to Factor VIII: 25 mM tris(hydroxymethyl)aminomethane, 4.2 mM calcium chloride, 8% (w/v) mannitol, 225 mM sodium chloride, 0.2 mg/mL glutathione, and 0.025% (w/v) polysorbate 80.

2. The composition of claim 1, further comprising 25 mM histidine.

3. The composition of claim 2, further comprising 2% (w/v) trehalose.

4. The composition of claims 1 to 3, wherein the pH is between 6 and 8.

5. A liquid Factor VIII composition without albumin, said composition comprising the following formulation excipients in addition to Factor VIII: 10 mM tris(hydroxymethyl)aminomethane, 1.7 mM calcium chloride, 0.08 mg/mL glutathione, and 0.01% (w/v) polysorbate 80.

6. The composition of claim 5, further comprising 10 mM histidine.

7. The composition of claim 6, further comprising 1% trehalose.

8. The composition of claim 7, further comprising 4% (w/v) mannitol.

9. The composition of claim 8, further comprising 100 mM sodium chloride.

10. The composition of any of claims 5 to 9, wherein the pH is between 6 and 8.

\* \* \* \* \*